(12) United States Patent
Dauster

(10) Patent No.: US 9,775,654 B2
(45) Date of Patent: Oct. 3, 2017

(54) SURGICAL RATCHET TOOL, SYSTEM AND METHOD

(71) Applicant: AESCULAP IMPLANT SYSTEMS, LLC, Center Valley, PA (US)

(72) Inventor: Andrew Dauster, Breinigsville, PA (US)

(73) Assignee: AESCULAP IMPLANT SYSTEMS, LLC, Center Valley, PA (US)

(*) Notice: Subject to any disclaimer, the term of this patent is extended or adjusted under 35 U.S.C. 154(b) by 892 days.

(21) Appl. No.: 13/839,262

(22) Filed: Mar. 15, 2013

(65) Prior Publication Data

US 2014/0277212 A1 Sep. 18, 2014

(51) Int. Cl.
| | |
|---|---|
| A61B 17/58 | (2006.01) |
| A61B 17/70 | (2006.01) |
| A61B 17/88 | (2006.01) |
| B25B 13/46 | (2006.01) |

(52) U.S. Cl.
CPC ...... *A61B 17/7086* (2013.01); *A61B 17/8875* (2013.01); *B25B 13/462* (2013.01)

(58) Field of Classification Search
CPC ............ A61B 17/8869; A61B 17/7086; A61B 17/8875; A61B 17/8891; A61B 19/301; B25B 13/462; B25B 23/1427; A61C 1/186; A61C 8/0089; B23Q 3/06
USPC ..... 81/60–63.2, 467, 477, DIG. 5; 606/86 R, 606/104–105, 102, 99–100; 40/334
See application file for complete search history.

(56) References Cited

U.S. PATENT DOCUMENTS

| | | | | |
|---|---|---|---|---|
| 5,653,151 | A | * 8/1997 | Blacklock | A61C 8/0089 81/438 |
| 5,709,137 | A | * 1/1998 | Blacklock | A61C 8/0089 81/467 |
| 5,996,453 | A | * 12/1999 | Blacklock | A61C 8/0089 81/467 |
| 6,948,605 | B1 | 9/2005 | Gauthier | |
| 6,988,430 | B1 | * 1/2006 | Putney | B25B 13/04 81/60 |

(Continued)

FOREIGN PATENT DOCUMENTS

| | | |
|---|---|---|
| EP | 1 834 734 A1 | 9/2007 |
| EP | 2 425 930 A1 | 3/2012 |
| GB | 2 318 535 A | 4/1998 |

OTHER PUBLICATIONS

Extended European search report for the related European Patent Application No. 14767511.0 dated Mar. 14, 2016.

*Primary Examiner* — Jessica Weiss
(74) *Attorney, Agent, or Firm* — Kenealy Vaidya LLP

(57) ABSTRACT

A surgical ratchet tool and system along with associated methods are disclosed. The surgical ratchet tool can include a relatively simple encompassing member that included a pawl extending into the opening for directly contacting a nut during surgery. The ratchet tool and system can be used for various types of surgery in which easy sterilization and a reduced profile for a ratchet tool is desired. For example, the ratchet tool can be used during surgery for adjustment of a spinal implant, where manipulation of a nut located on a downtube connected to a screw and/or spinal rod is desired. The encompassing member and pawl can be constructed/molded as a single piece unitary structure. A first handle and possibly a second handle can extend from an outer periphery of the encompassing member.

23 Claims, 13 Drawing Sheets

(56) References Cited

U.S. PATENT DOCUMENTS

| | | |
|---|---|---|
| 7,194,934 B2 | 3/2007 | Abdelgany |
| 7,363,838 B2 | 4/2008 | Abdelgany |
| 7,597,032 B2 * | 10/2009 | Baumgartner ........ B25B 13/463 81/467 |
| 7,895,724 B1 * | 3/2011 | Dugan .................... B25B 13/04 29/407.01 |
| 7,913,594 B2 | 3/2011 | Gauthier et al. |
| 8,100,913 B2 | 1/2012 | Abdelgany |
| 8,123,785 B2 | 2/2012 | Weaver et al. |
| 8,206,394 B2 | 6/2012 | Stad et al. |
| 2010/0212460 A1 | 8/2010 | Buss et al. |
| 2012/0060652 A1 * | 3/2012 | Gapp ...................... B25B 13/08 81/58.2 |
| 2013/0030445 A1 | 1/2013 | Dauster et al. |

* cited by examiner

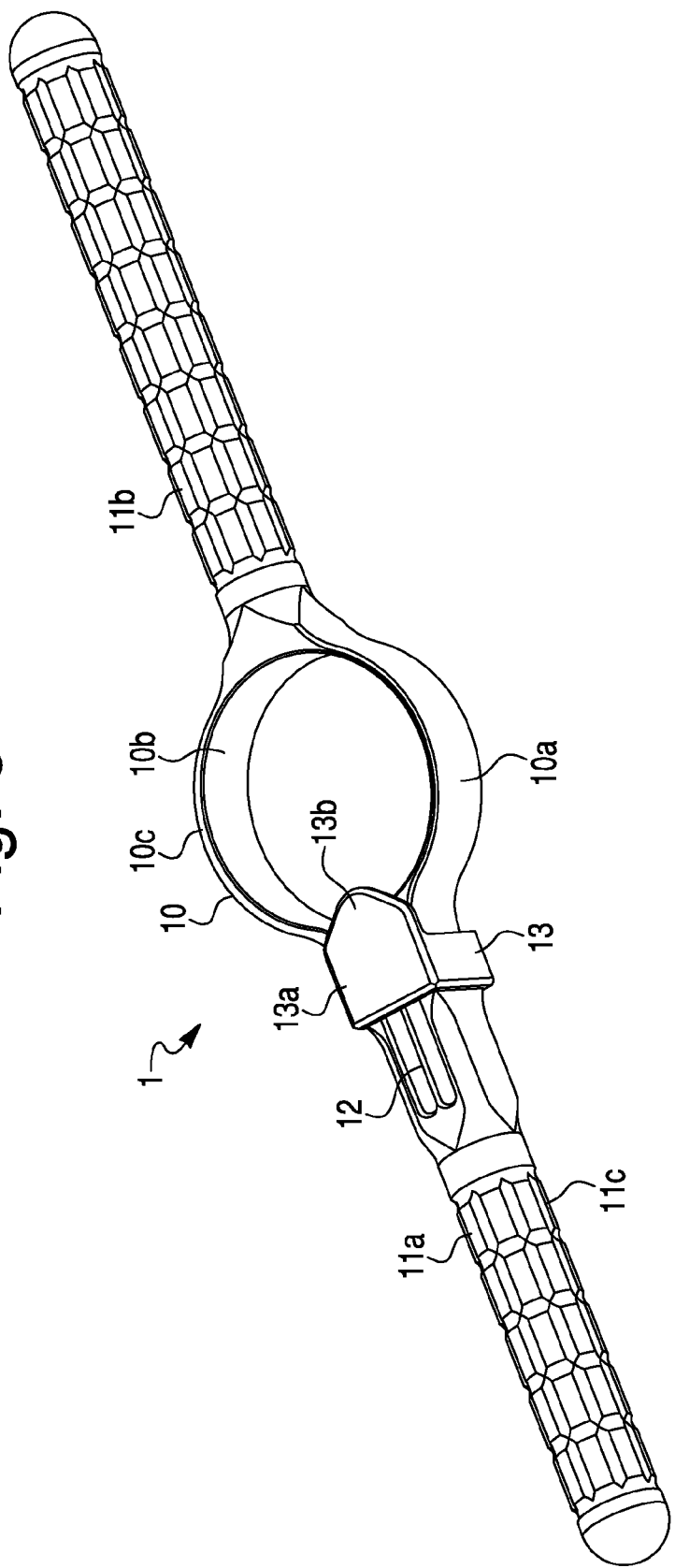

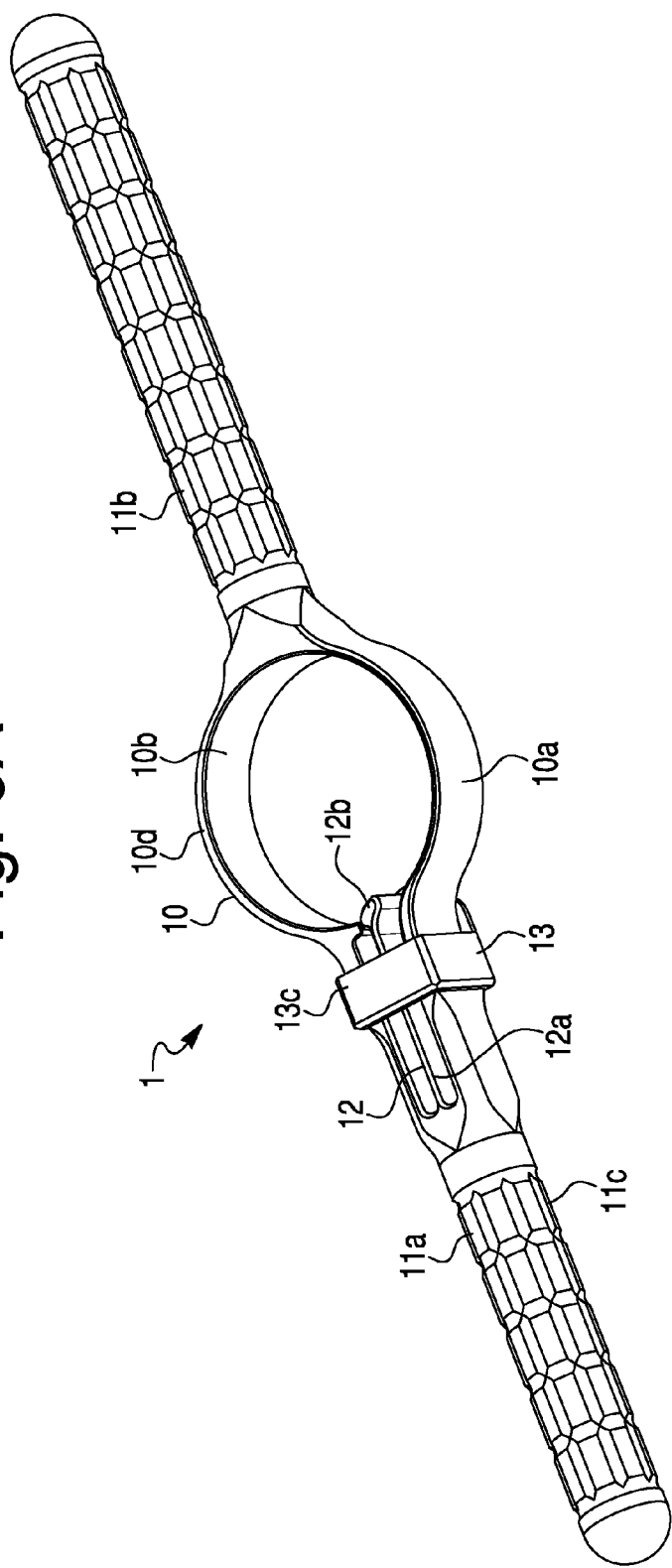

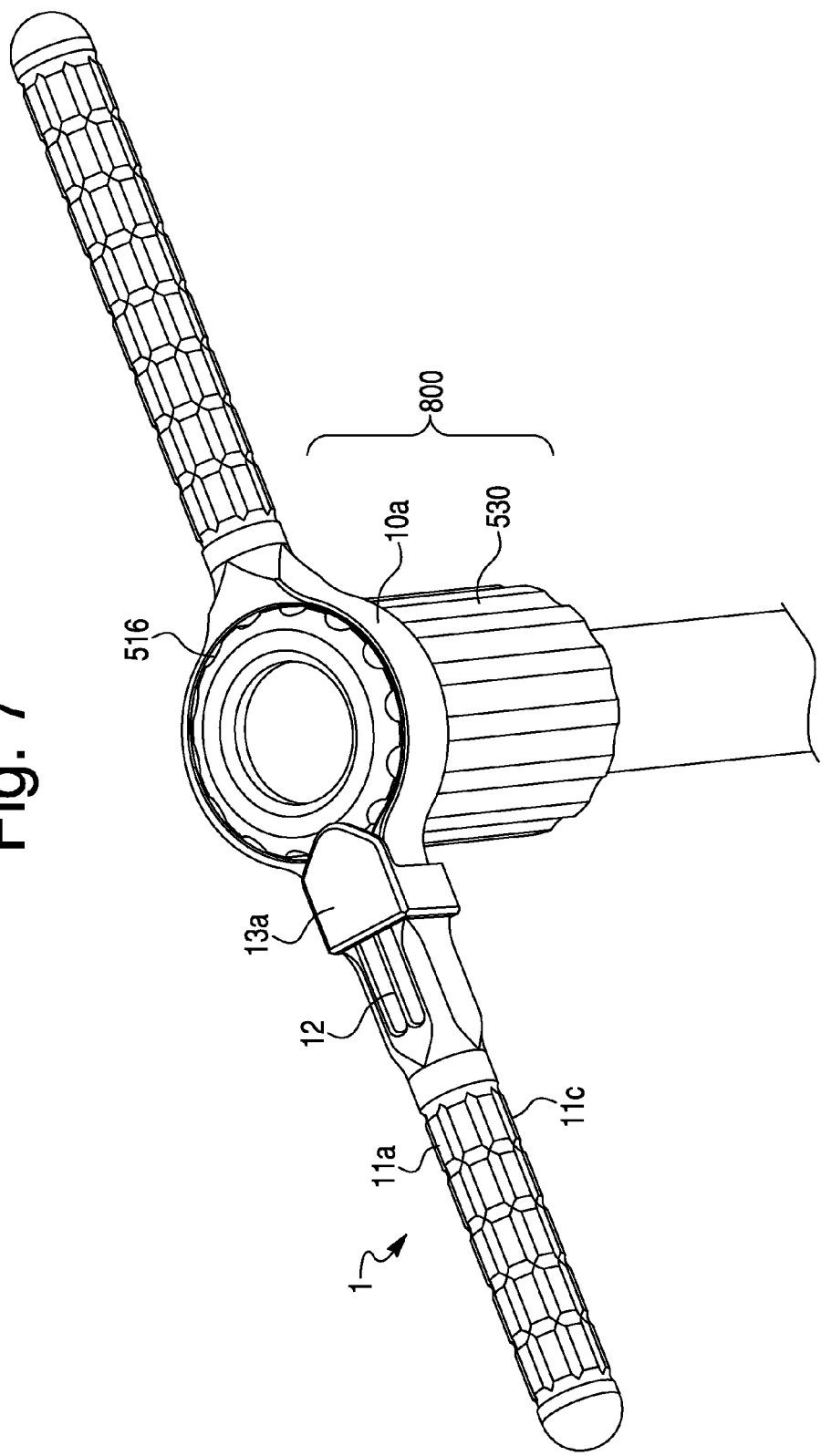

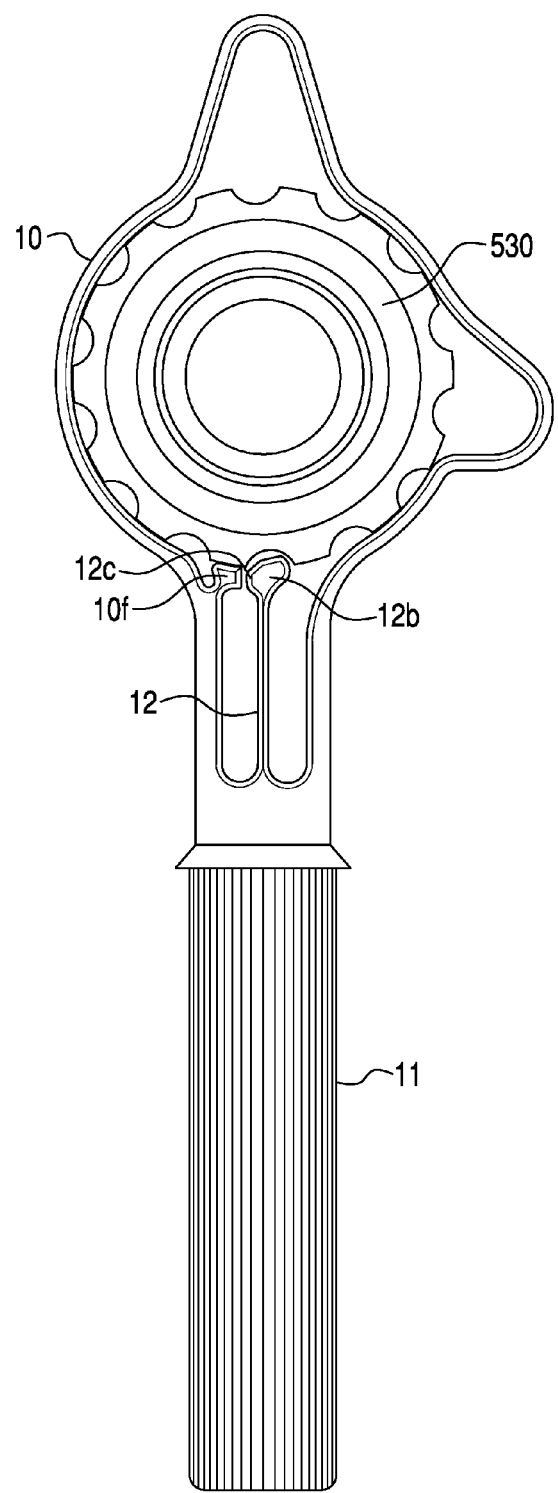

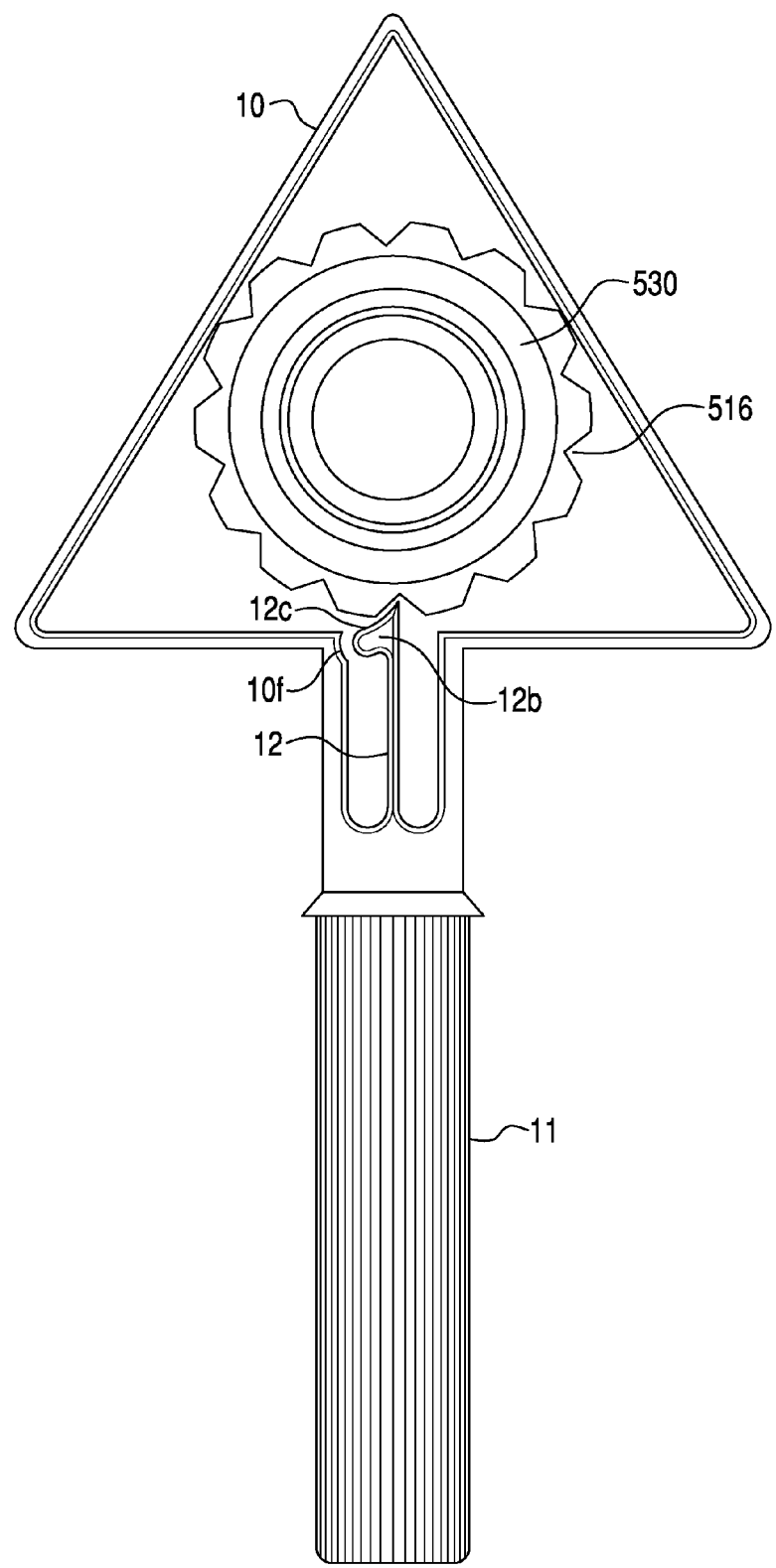

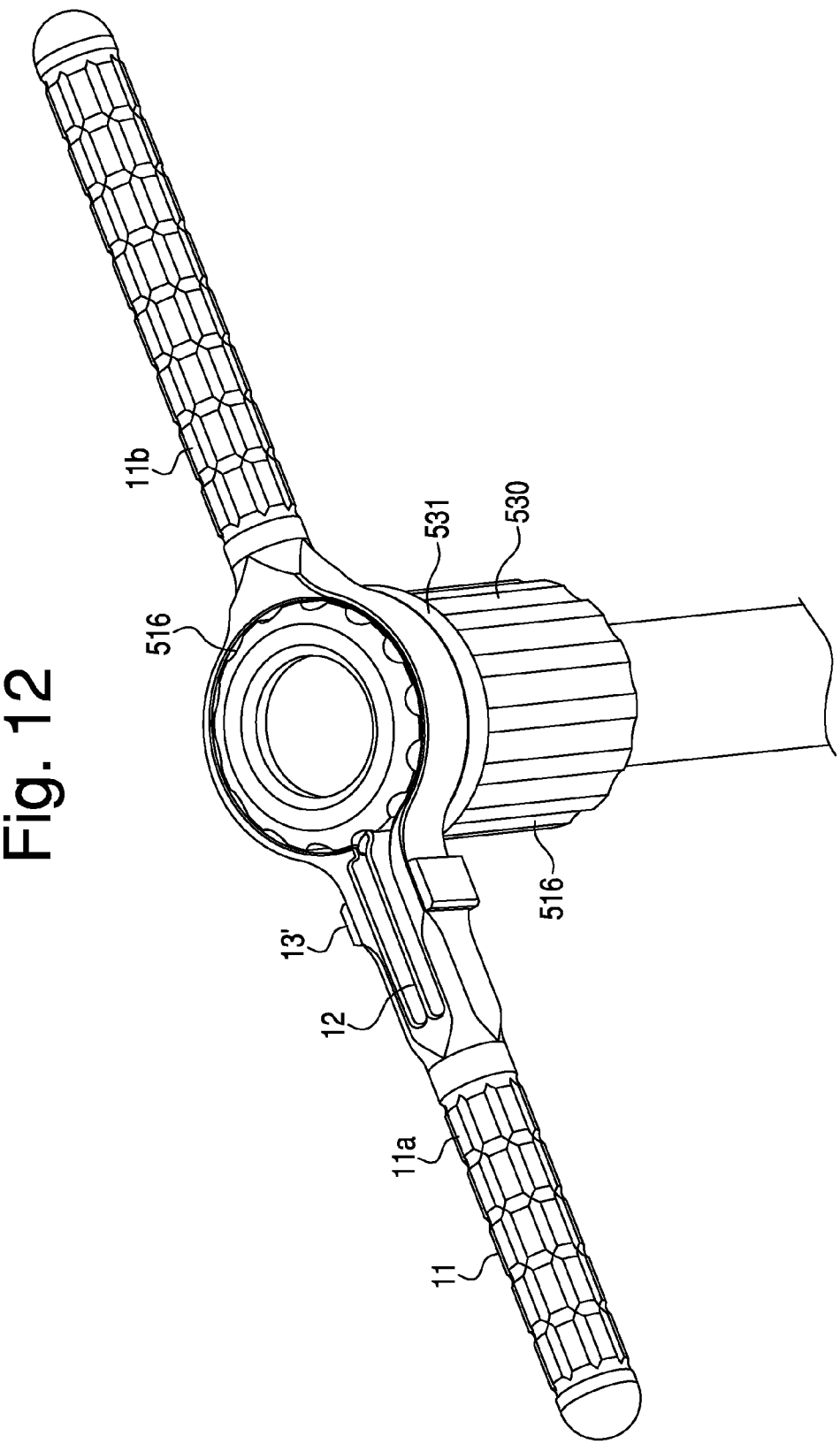

SURGICAL RATCHET TOOL, SYSTEM AND METHOD

BACKGROUND

1. Field

The presently disclosed subject matter relates generally to surgical instrumentation and related methods, and more specifically to ratchet tools for applying torque to a surgical tool, surgical implement, implant or other device used during a surgical procedure or other procedures requiring a torque.

2. Description of the Related Art

There are several occasions in the surgical field that call for the use of a ratchet tool. Typically, a ratchet tool is desired when torque is being applied to another tool, implant, or other surgical device, and the space defining the surgical field is limited. Additionally, ratchet tools are sometimes helpful to decrease the time necessary for completing a particular action or procedure. For example, a ratchet tool can be used to avoid continual removal and reinstallation of a typical standard set wrench.

Known ratchet tools include those used with bone screws, drivers, persuaders, and other structures that require application of torque during surgery. Typically, known ratchet tools are similar to those found in any automotive repair garage. Specifically, known ratchet tools usually include a cylinder that houses a raceway including bearings and a ratchet/pawl mechanism that is biased by a spring. Thus, typical ratchet tools include a number of individual parts that are manufactured or machined, and which are then assembled together to form the ratchet tool. Many ratchet tools include bearings and bearing surfaces, and some have a lubricant that facilitates rotation and relative movement between the separate parts of the known ratchet tool.

It is sometimes crucial for surgeons to monitor a bone screw, spinal rod, or other device as it is being driven into or moved relative to a bone or other tissue. Surgeons typically avoid overtightening or excessively moving the screw or rod, etc., because such an action may cause damage to the bone, tissue, or misalignment of the bone and/or tissue, etc. When surgeons insert and tighten bone screws, rods, etc., via an extender type mechanism, such as a downtube, it may be difficult to visually monitor the screw, rod, or other device to know if it is being overtightened or misaligned. Therefore, surgeons often rely on "feel" or tactile feedback to monitor their progress in driving the screw, rod, or other device for movement or placement relative to a bone or other tissue. Thus, the surgical instrument that is driven is typically rigidly attached to a downtube (or other extender mechanism) in a way that minimizes or prevents "play" or toggle between the driver and downtube. Even a small amount of toggle between the driver and downtube can prevent a surgeon from sensing tactile feedback during a procedure. Thus, the tolerance and fit for the ratchet tool with respect to the surgical instrument, implant or device it is driving is also an important aspect of ensuring that "play" or toggle is minimized during the surgical procedure.

Characteristics and drawbacks of known ratchet tools include a complicated assembly and manufacture process, resulting in a relatively expensive device/tool in terms of both manufacturing cost and parts/material cost. In addition, known ratchet tools are often difficult to sterilize due to their complicated structure. In some cases, the ratchet tool has poor fit and has multiple stationary teeth that move in and out of engagement during ratcheting operation, resulting in play or toggle which has the complications as outlined above.

SUMMARY

Accordingly, there has been a long felt need for ratchet tools, systems and methods that are simple in design with a minimal number of parts, allowing for efficient sterilization, while also small in overall space/profile for use in a limited surgical field, and which have tolerances and efficiencies that facilitate a speedy surgical operation.

According to one aspect of the disclosure, a surgical ratchet tool can include an encompassing member which can include an arcuate or partially arcuate surface having an inner peripheral surface, an outer peripheral surface opposed to the inner peripheral surface, a top surface, and a bottom surface opposed to the top surface. The encompassing member can define an opening that has a central axis extending therethrough. The encompassing member can define a closed loop, such as a circular, polygonal, non-symmetrical, or other type of cylinder, but can also have an open shape, for example, a C-shape, Y-shape, or generally open configuration instead of a closed loop configuration. The ratchet tool can include at least one handle extending from the outer peripheral surface of the encompassing member, and a pawl located within the handle. The pawl can have a spring (or biased) portion with a proximal end and a distal end, and a head located at the distal end of the spring portion. The proximal end of the spring portion can be connected to the handle such that the head of the pawl is movable with respect to at least one of the handle and the encompassing member.

According to another aspect of the disclosure, a surgical ratchet tool can include an encompassing member having an inner peripheral surface, an outer peripheral surface opposed to the inner peripheral surface, a top surface, and a bottom surface opposed to the top surface. The encompassing member can define an opening that has a central axis extending therethrough, and can have a longitudinal axis running about an extent of the encompassing member. The ratchet tool can be provided with a pawl including a head and a spring structure, the pawl having a longitudinal axis that intersects with the longitudinal axis of the encompassing member such that at least a portion of the head structure is located on a an interior side of a plane that contains an immediately adjacent portion of the inner peripheral surface of the encompassing member while at least a portion of the spring structure is located on an exterior side of a plane that contains an immediately adjacent portion of the outer peripheral surface of the encompassing member. At least one handle can extend from the outer peripheral surface of the encompassing member. However, additional handles can be included, including a handle that is coaxial with the first handle, or a handle (or handles) that has a longitudinal axis that is at an acute or oblique angle with respect to a longitudinal axis of the first handle.

According to another aspect of the disclosure, a surgical tool system can include a ratchet tool and a nut for use with the ratchet. The ratchet tool can include an encompassing member having an inner peripheral surface, and an outer peripheral surface opposed to the inner peripheral surface, the encompassing member defining an opening that has a central axis extending therethrough. The ratchet tool can include a pawl that has a head and a spring structure, and at least a portion of the head structure can be located within the opening of the encompassing member. The ratchet tool can also include at least one handle extending from the outer peripheral surface of the encompassing member. The nut can include an outer peripheral surface that has a plurality of indents configured to receive the head of the pawl therein, wherein the pawl is configured such that during operation of the ratchet tool the head of the pawl moves with respect to both the handle and encompassing member such that the pawl releases from the nut and allows the ratchet tool to rotate with respect to the nut in a first rotational direction, while remaining in contact with the nut and requiring the ratchet tool to rotate with the nut in a second rotational direction opposite the first rotational direction.

According to another aspect of the disclosure, a method of using a surgical wrench can include beginning a surgical procedure on a body, and providing a surgical wrench having a main body having an inner peripheral surface defining an opening with a central axis. The main body can include a pawl that extends into the opening of the main body of the surgical wrench. The method can include providing a nut that includes at least one ratchet indent located on an outer periphery of the nut, and placing the surgical wrench onto the nut such that the nut is located within the opening of the surgical wrench. The method can further include directly contacting the at least one ratchet indent of the nut with the pawl of the surgical wrench and rotating the surgical wrench such that the nut rotates with the surgical wrench in a first rotational direction, and rotating the surgical wrench in a second rotational direction opposite to the first rotational direction while causing the pawl to flex or bias with respect to the main body and nut such that the surgical wrench rotates with respect to the nut.

According to yet another aspect of the disclosure, a method of manufacturing a surgical ratchet tool can include providing a mold that includes a first cavity portion defining an encompassing member, a second cavity portion defining a handle, and a third cavity portion defining a pawl. The third cavity portion can be at least partially located within the second cavity portion. The method can include pouring a material into the mold so as to substantially fill the first cavity, second cavity and third cavity, and allowing the material located within the mold to harden. The method can then include removing the material after hardening such that the hardened material forms the surgical ratchet tool including a handle, encompassing member, and pawl.

According to still another aspect of the disclosed subject matter, a surgical ratchet can include an encompassing member having an inner peripheral surface, an outer peripheral surface opposed to the inner peripheral surface, and an opening. A first handle can extend away from the outer peripheral surface of the encompassing member, the handle having a proximal end and a distal end opposite the proximal end with a longitudinal axis extending therebetween. The distal end of the first handle being connected to the outer peripheral surface of the encompassing member. A pawl can have a fixed end attached to the distal end of the first handle, the pawl extending away from the first handle and extending into the opening which is defined by the inner peripheral surface and the distal end of the first handle. The pawl can have a biased portion and a head located at a free end opposite the fixed end. The biased portion of the pawl can be disposed between first and second opposing portions of the inner peripheral surface, wherein the head is movable with respect to at least one of the first handle and encompassing member.

According to yet another aspect of the disclosed subject matter, a surgical ratchet can include an encompassing member having an inner peripheral surface, an outer peripheral surface opposed to the inner peripheral surface, and an opening. A first handle can extend away from the outer peripheral surface of the encompassing member, the handle having a proximal end and a distal end opposite the proximal end with a longitudinal axis extending therebetween. A pawl can have a fixed end attached to the first handle at a location intermediate the proximal and distal ends of the first handle, the pawl extending into the opening which is defined by the inner peripheral surface and the first handle. The pawl can also have a biased portion and a head located at a free end opposite the fixed end, the biased portion of the pawl disposed between first and second opposing portions defined at the distal end of the first handle. The first and second opposing portions of the first handle can be connected to the inner peripheral surface of the encompassing member, and the distal end of the first handle can be connected to the outer peripheral surface of the encompassing member at an outer surface of the first handle. The head can be movable with respect to at least one of the first handle and encompassing member.

According to still another aspect of the disclosed subject matter, the pawl longitudinal axis and the encompassing member has a member longitudinal axis, wherein the pawl longitudinal axis intersects with the member longitudinal axis.

According to another aspect of the disclosed subject matter, the handle, the pawl, and the encompassing member are made from a single continuous unitary material. The handle, the pawl, and the encompassing member can be formed via a molding process, or can be machined, or formed using other known manufacturing methods.

According to another aspect of the disclosed subject matter, a band can be connected to a first portion of the handle located on a first side of the pawl, the band extending over the pawl and connected to a second portion of the handle located on a second opposite side of the pawl. The band can include an extension portion that extends into the opening of the encompassing member from the top surface of the encompassing member.

According to another aspect of the disclosed subject matter, the pawl can extend into the opening of the encompassing member from a position located between a first portion of the encompassing member and a second portion of the encompassing member, the first portion being spaced from the second portion to define a pawl accessway therebetween, and the pawl intersecting the pawl accessway located between the first portion and second portion of the encompassing member. The band can be connected between the first portion and the second portion of the encompassing member and can extend over the pawl to connect the first portion to the second portion of the encompassing member. The pawl can be configured as a planar sheet of material having an enlarged portion defining the head at the distal end of the pawl.

According to still another aspect of the disclosed subject matter, the at least one handle can have a handle longitudinal axis, and the handle longitudinal axis can be substantially parallel with or coaxial with the pawl longitudinal axis.

According to still another aspect of the disclosed subject matter, a surgical tool system can include a ratchet tool and a nut. The ratchet tool can include an encompassing member having an inner peripheral surface, and an outer peripheral surface opposed to the inner peripheral surface, the encompassing member defining an opening that has a central axis extending therethrough. The ratchet tool can further include a pawl including a head and a spring structure, at least a portion of the head structure being located within the opening of the encompassing member, and at least one handle extending from the outer peripheral surface of the encompassing member. The nut can include an outer peripheral surface that has a plurality of indents configured to receive the head of the pawl therein. The pawl can be configured such that during operation of the ratchet tool the head of the pawl moves with respect to at least one of the handle and encompassing member such that the pawl releases from the nut and allows the ratchet tool to rotate with respect to the nut in a first rotational direction, while remaining in contact with the nut and requiring the ratchet tool to rotate with the nut in a second rotational direction opposite the first rotational direction.

According to another aspect, the surgical tool system can further include a downtube having a proximal end and a distal end, the nut located at the proximal end of the downtube, and a surgical structure located at the distal end of the downtube. The nut and downtube can be configured to transmit at least one of rotational motion and translational motion to the surgical structure located at the distal end of the downtube when rotational motion in a first direction is imparted to the nut via the ratchet tool. The surgical structure can possibly be a bone screw, a spinal rod, a polyaxial pedicle screw for a spine, or other surgical medical structure. The nut can be located at a proximal end of a bone screw. The ratchet tool can include a second handle extending from the outer peripheral surface of the encompassing member.

According to another aspect of the disclosed subject matter, the surgical tool system can include a pawl that has a pawl longitudinal axis and the encompassing member can have a member longitudinal axis, wherein the pawl longitudinal axis intersects with the member longitudinal axis. The surgical tool system can also include a pawl that has a pawl longitudinal axis and the at least one handle can have a handle longitudinal axis, and the handle longitudinal axis can be one of substantially parallel and coincident or coaxial with the pawl longitudinal axis.

According to another aspect of the disclosed subject matter, the surgical tool system can be configured such that the handle, the pawl, and the encompassing member are made from a single continuous unitary material, and the handle, the pawl, and the encompassing member are formed via a molding process.

According to another aspect of the disclosed subject matter, the surgical tool system can further include a band connected to a first portion of the handle located on a first side of the pawl, and the band can extend over the pawl and be connected to a second portion of the handle located on a second opposite side of the pawl. The ratchet tool can be made from at least one of titanium and stainless steel.

According to another aspect of the disclosed subject matter, a method of using a surgical wrench can include beginning a surgical procedure on a body, providing a surgical wrench having a main body with an inner peripheral surface defining an opening having a central axis, the main body including a pawl that extends into the opening of the main body of the surgical wrench, providing a nut that includes at least one ratchet indent located on an outer periphery of the nut, placing the surgical wrench onto the nut such that the nut is located within the opening of the surgical wrench, directly contacting the at least one ratchet indent of the nut with the pawl of the surgical wrench, rotating the surgical wrench such that the nut rotates with the surgical wrench in a first rotational direction, and rotating the surgical wrench in a second rotational direction opposite the first rotational direction while causing the pawl to flex or bias with respect to at least one of the main body and the nut such that the surgical wrench rotates with respect to the nut.

According to another aspect of the disclosed subject matter, the nut of the method can include a plurality of ratchet indents located about the outer periphery of the nut, and rotating the surgical wrench in a second rotational direction can include causing the pawl to flex or bias into and out of the plurality of ratchet indents such that the nut remains stationary while the surgical wrench rotates with respect to the nut. Rotating the surgical wrench in the second direction can occur one of prior to and after rotating the surgical wrench in the first direction. The nut can be connected to a downtube which is connected to a pedicle screw attached to a human spine, and the method can further include adjusting a position of a rod associated with the pedicle screw located in the human spine by rotating the surgical wrench in the first rotational direction. The method can further include providing a persuader that is rotatably attached to the nut, providing a downtube having a distal end and a proximal end, positioning the distal end of the downtube adjacent a spine via a puncture incision, and locating the persuader in the downtube and adjacent a spinal rod, wherein rotating the surgical wrench in the first rotational direction causes the persuader to move the spinal rod.

According to still another aspect of the disclosed subject matter, the method of manufacturing a surgical ratchet tool can further include attaching a support band to at least one of the handle and the encompassing member, by welding or by use of additional attachment structure(s) or attachment material(s). The method can include contacting the pawl directly with a nut to confirm operability of the tool. The method can also include providing a fourth cavity portion defining a second handle, and pouring the material into the mold so as to substantially fill the fourth cavity.

BRIEF DESCRIPTION OF THE DRAWINGS

The disclosed subject matter of the present application will now be described in more detail with reference to exemplary embodiments of the apparatus, system, and methods, given by way of example, and with reference to the accompanying drawings, in which:

FIG. 5 is a top perspective view of a ratchet tool made in accordance with principles of the disclosed subject matter;

FIG. 6A is a bottom perspective view of the ratchet tool of FIG. 5;

FIG. 7 is a perspective top view of the ratchet tool of FIG. 5 used in a system in accordance with principles of the disclosed subject matter;

FIG. 10 is a perspective view of another embodiment of a system, including a ratchet tool and nut, made in accordance with principles of the disclosed subject matter;

FIG. 11 is a perspective view of another embodiment of a portion of a system, including a ratchet tool and nut, made in accordance with principles of the disclosed subject matter;

FIG. 12 is a perspective view of another embodiment of a portion of a system, including a ratchet tool and nut, made in accordance with principles of the disclosed subject matter;

DETAILED DESCRIPTION OF EXEMPLARY EMBODIMENTS

The following is a description of the various drawings which depict specific exemplary embodiments of the disclosed subject matter. It will be apparent to one skilled in the art that various changes can be made, and equivalents employed, without departing from the scope of the disclosed subject matter. In that regard, the drawings make particular reference to a system for use in surgery on the spine, and in particular to the use in minimally invasive surgery for inserting and/or adjusting spinal rod components. However, it should be understood that the disclosed subject matter can be equally applicable to other types of surgery, including general and orthopedic surgery in which application of torque is required to be applied to a tool, implant, or other surgical structure located in a limited surgical field.

Figure 1:
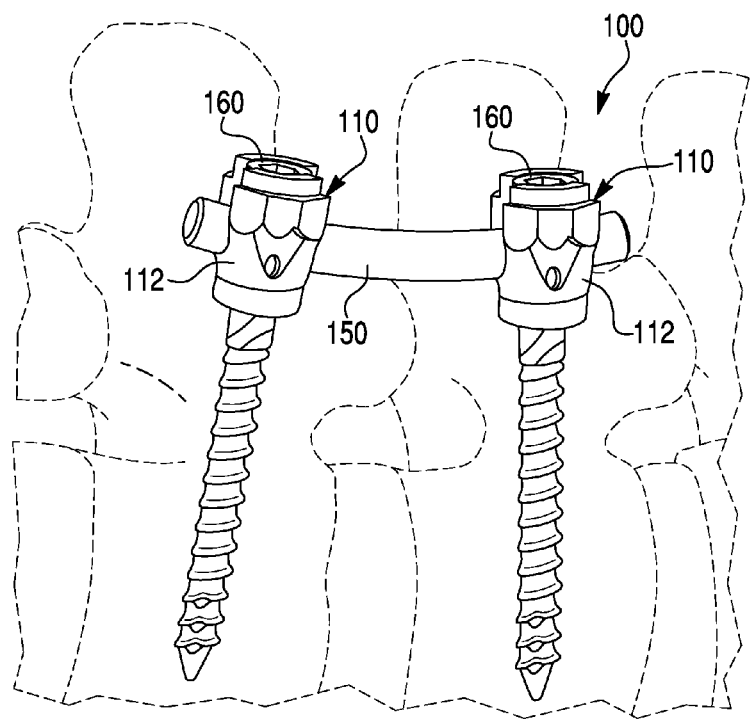
FIG. 1 is a perspective view of a portion of a system, including a screw and rod fixation assembly for use with a ratchet tool, made in accordance with principles of the disclosed subject matter.

FIG. 1 is a perspective view of a portion of an exemplary system, including a screw and rod fixation assembly 100 for use with a ratchet tool 1, made in accordance with principles of the disclosed subject matter. Fixation assembly 100 includes two surgical screw assemblies 110. Each screw assembly 110 has a U-shaped head 112 with a threaded opening and a channel for receiving an elongated fixation member or rod 150. Rod 150 can be locked into the screw assemblies 110 by set screws 160 (which are screwed into the threaded openings located at the top of the U-shaped portion of the heads 112) after the rod 150 is properly positioned in each of the heads. The rod 150 and set screws 160 can be introduced into the screw assemblies 110 through the use of a downtube 200.

Figure 2:
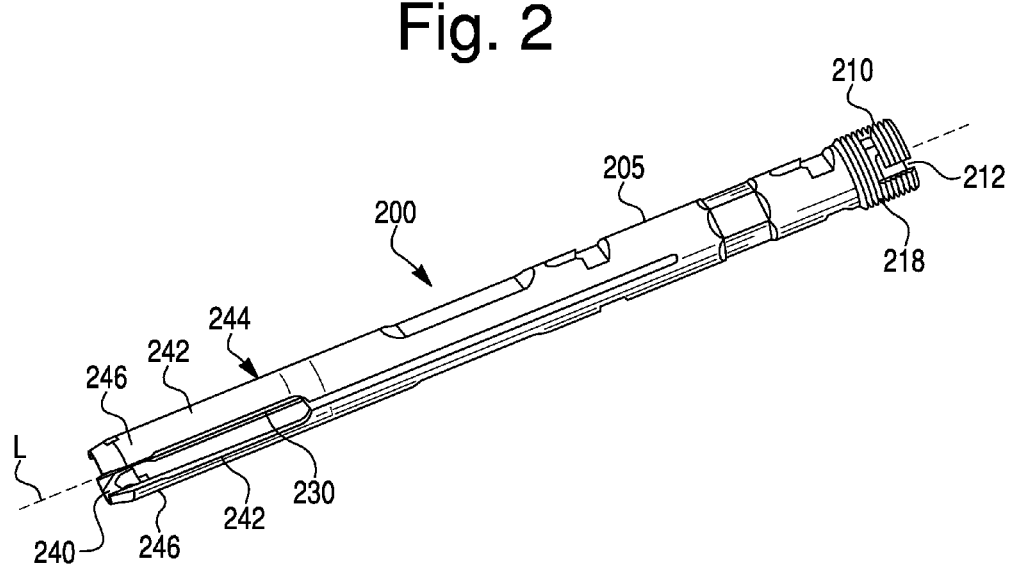
FIG. 2 is a perspective view of a downtube for use in the system of FIG. 1.

FIG. 2 shows one example of a downtube 200 made in accordance with principles of the disclosed subject matter. The downtube 200 functions as a temporary extension for screw assemblies 110, forming a conduit to the surgical site. The downtube 200 can include a hollow tubular body 205 having a proximal end 210, a distal end 240 opposite the proximal end, and a hollow passage 230 extending between the proximal end and distal end. Proximal end 210 forms an opening 212 sized to receive various other instrumentation, which will be described in more detail below. The distal end 240 includes a pair of attachment members 242 for attaching to the screw assemblies 110. However, as indicated above, the downtube 200 can work with many different types of surgical tools, implants, attachment structures, and devices. The attachment members 242 collectively form a clamping mechanism 244 that securely attaches the downtube 200 to the screw assemblies 110. Clamping mechanism 244 works by elastic deformation of the attachment members 242.

The downtube 200 can be assembled from multiple parts formed of different materials or can be constructed as one single homogeneous body of material, rather than an assembly of parts. The material selected for the downtube 200 can provide for sufficient elasticity at the attachment members 242. In addition, the material can be a biocompatible material. Suitable materials include but are not limited to stainless steel, titanium, other metals, metal alloys, ceramics, plastics, or superelastic shape memory alloys like Nitinol, or combinations thereof. Each attachment member 242 includes an arm 246 having a bearing surface facing into passage 230. Each bearing surface can include an engagement element for attachment to a screw assembly 110. A variety of engagement elements can be used, including but not limited to bosses or detents, which may be fixed or deflectable. In the case of deflectable elements, the elements may be spring biased to project into passage 230, and retractable against the spring bias into the arms.

Figure 3:
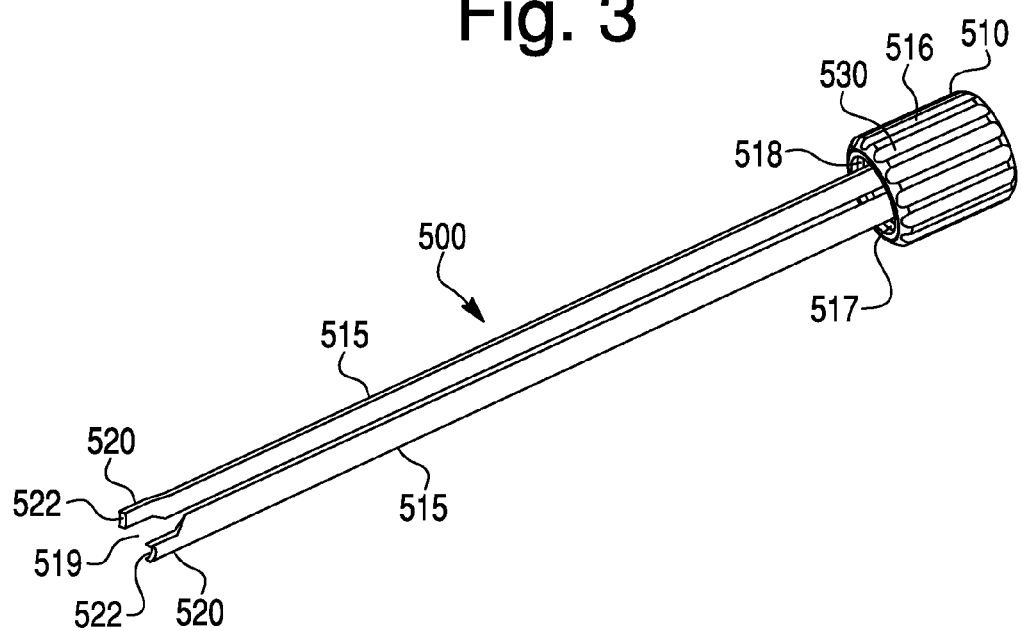
FIG. 3 is a perspective view of a rod persuader for use in the system of FIG. 1.

FIG. 3 is a perspective view of an exemplary rod persuader 500 for use with the downtube 200 as described above. The rod persuader 500 can include a proximal end 510 and a pair of pusher members 515. Pusher members 515 can be separated by a central opening 519 and coaxially aligned with the longitudinal axis L of downtube 200.

Figure 4:
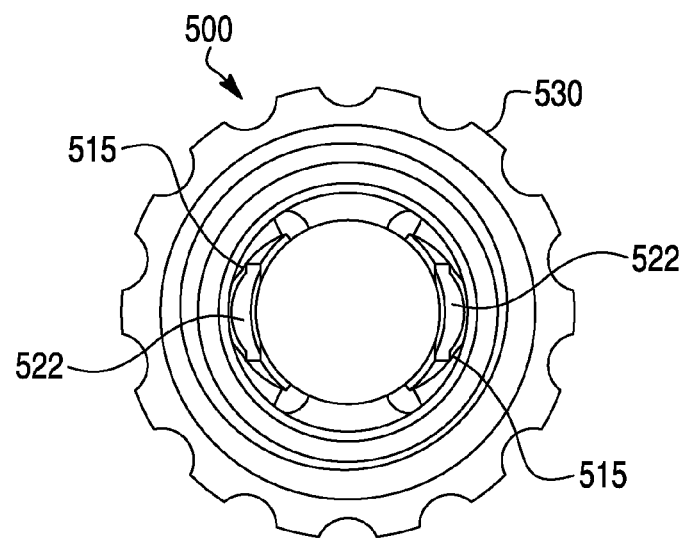
FIG. 4 is a top view of the rod persuader of FIG. 3.

Each pusher member 515 can include a distal end 520 with a notch 522 to fit about the contour of fixation rod 150. A nut can be rotatably coupled to the pusher members 515. In this example, the nut is configured as a hollow cylindrical knob 530 that includes a knurled exterior surface 516 and an interior surface 517. Interior surface 517 can include an inner thread 518 adapted to engage with the outer thread 218 on downtube 200. FIG. 4 is a top view of the rod persuader 500 and shows the knurled surface 516 as well as the relationship between the knob 530 and pusher members 515 in greater detail.

During use, once the rod persuader 500 is inserted into passage 230 of downtube 200, knob 530 can be screwed down over the proximal end 210 of the downtube to rigidly attach the rod persuader to the downtube, with little or no toggle or play. After knob 530 is threaded onto outer thread 218, the knob can be further rotated to axially advance the pusher members 515 into engagement with rod 150 and push the rod into a desired position in the screw assembly 110. This further rotation of the knob 530 can be accomplished using a ratchet tool 1.

FIG. 5 is a top perspective view of an exemplary ratchet tool 1 that can be used to rotate a nut, such as knob 530, to achieve smooth and efficient torque transfer during a surgical procedure. The ratchet 1 can include an encompassing member 10 having an inner peripheral surface 10b, an outer peripheral surface 10a opposed to the inner peripheral surface 10b, a top surface 10c, and a bottom surface 10d opposed to the top surface 10c. The encompassing member 10 can define an opening having a central axis extending therethrough. The central axis can be substantially parallel with the outer peripheral surface 10a and inner peripheral surface 10b (and can be substantially perpendicular to the top surface 10c and/or bottom surface 10d if/when either of these surfaces is substantially flat). The encompassing member 10 can have a longitudinal axis running about an extent of the encompassing member. The longitudinal axis can be substantially parallel with the outer peripheral surface 10a and inner peripheral surface 10b when these surfaces are configured as a cylinder, and can also be substantially parallel with the top surface 10c and/or bottom surface 10d.

The ratchet tool 1 can include a handle 11a extending from the outer peripheral surface 10a of the encompassing member 10. The handle 11a can include a knurled surface 11c to provide for a non-slip gripping surface for the user. In the present embodiment, a pawl 12 is located in a distal portion of the handle 11a that is immediately adjacent the encompassing member 10. A second handle 11b can extend from the outer peripheral surface 10a of the encompassing member 10 at a location directly opposed to the first handle 11a such that a longitudinal axis for each handle is coincident (coaxial) with each other. Of course, the second handle 11b could also extend obliquely or orthogonal with respect to the handle 11a and have various shapes, including arcuate or bent shapes. Moreover, the handle 11b can be configured to be identical to handle 11a, or can be sized and shaped differently depending on application and desire of the user.

The encompassing member 10 has an opening that defines an accessway in which the pawl 12 resides (as described in greater detail below). A band 13 can be attached to the encompassing member 10 (or possibly to the handle 11) at either side of the accessway for the purpose(s) of, for example, reinforcing and strengthening the encompassing member 10, ensuring proper accessway to pawl 12 such that the space between the pawl 12 and the walls of the handle 11 (or between the opposing sides of the encompassing member and the pawl 12) is maintained constant such that consistent operation of the pawl 12 can be maintained, among other reasons. In addition, when the above-referenced space is maintained constant, machining, molding, or otherwise manufacturing the tool can be accomplished at lower tolerances, if desired. The band 13 can be configured to span over the pawl 12 (without contacting the pawl 12) and can include an outer edge 13b. The outer edge 13b extends into the opening defined by encompassing member 10 when viewed from a distance spaced from the encompassing member 10 along its central axis. The outer edge 13b can be configured to cover the pawl 12 from view for protection, as shown in the present embodiment, but can also have different shapes, such as a Y-shaped split, that would allow a surgeon or user to view the pawl 12 in operation during use (while also providing a contact surface for abutment against a top surface of the knob 530 when in use).

The material selected for the ratchet tool 1 can be any known biocompatible material(s). Suitable materials include but are not limited to stainless steel, titanium, other metals, metal alloys, ceramics, plastics, or superelastic shape memory alloys like Nitinol, or combinations thereof.

FIG. 6A is a bottom perspective view of the ratchet tool 1 which shows a bottom portion of the band 13 extending over the accessway in which the pawl 12 resides. The handle 11a can define the accessway at this location and the band 13 can be connected to either side of the handle 11a. The top portion 13a of the band 13 can extend over a top of the accessway at a portion where the accessway is defined by both the opposing portions of the handle 11a and opposing portions of the encompassing member 10. In this view, the outer edge 13b can more clearly be seen extending into the opening defined by the encompassing member 10.

Figure 6B:
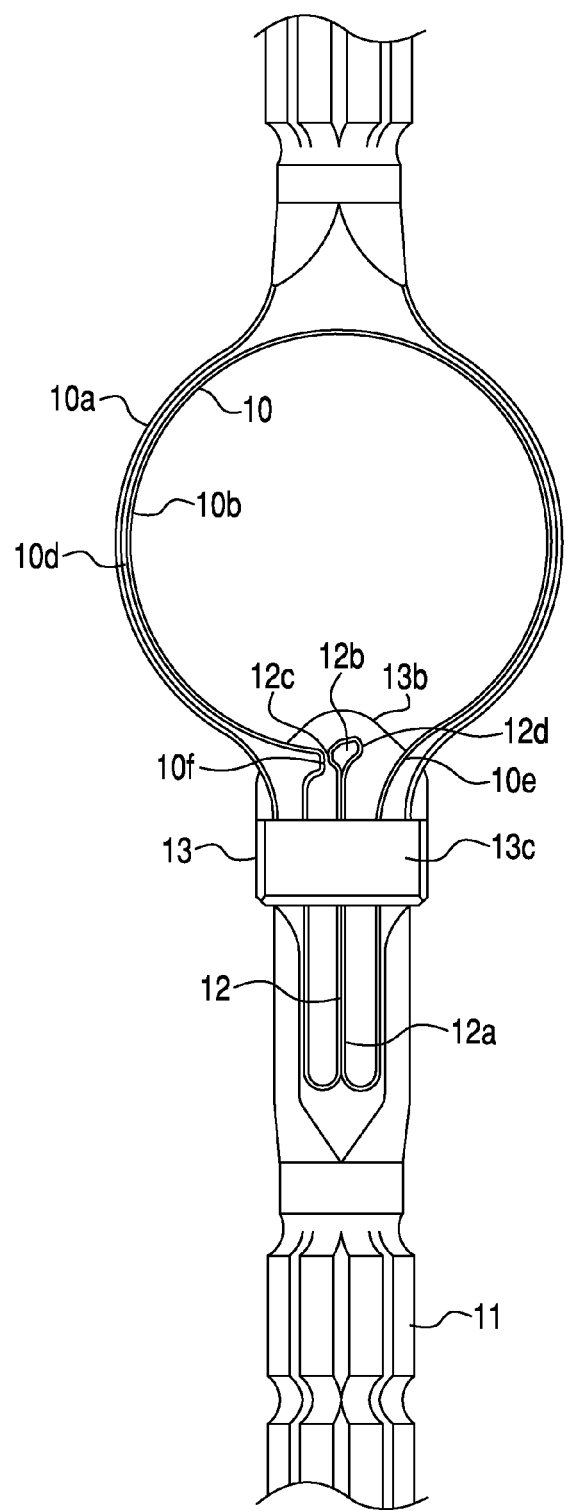
FIG. 6B is a bottom detailed view of the ratchet tool of FIG. 6A.

FIG. 6B is a bottom detailed view which shows the pawl 12 including a spring portion 12a and a head 12b. The spring portion 12a can be configured as a plate like structure attached to the handle 11a at a proximal portion of the spring portion 12a, and which terminates at head 12b located at a distal most portion of the spring portion 12a. The spring portion 12a can reside within walls of the handle 11 which extend substantially parallel with the spring portion 12a. The spring portion 12a is biased between opposing walls defining the accessway portion between the opening toward and away from the opposing walls. The spring portion 12a can be configured such that it is relatively easily bent about an axis located approximately at the proximal most portion of the spring portion 12a (for example, at the location of connection of the pawl 12 to the handle 11). Thus, the head 12b of the pawl 12 can move relative to the encompassing member 10 (and relative to the handle 11).

The head 12b can be configured to include a substantially (i.e., totally or almost totally) flat surface that engages with a contacting portion 10f of the encompassing member 10. As will be explained in more detail below, the contacting portion 10f of the encompassing member 10 will prevent the head 12b from moving in a first direction (i.e., substantially upwards in FIG. 6B). A rounded portion 12d of the head 12b is configured to extend into and engage an engaging surface defined by a nut, such as scalloped or knurled surfaces 516 of knob 530. The head 12b is substantially free to move in a second direction (i.e., substantially downwards in FIG. 6B).

The bottom surface 13c of band 13 can extend over the pawl 12 and connect the bottom surfaces of above-described walls of the handle 11 to ensure that walls remain stationary with respect to each other and to prevent flexing of the opposed portions 10e and 10f of the encompassing member 10.

FIG. 7 shows the ratchet tool 1 used with a nut, which in this embodiment is shown as a knob 530 used in conjunction with a downtube 200. In operation, the ratchet tool 1 can be placed over the knob 530 such that the knob fits within the opening of the encompassing member 10. In this case, the rotational axis of the knob 530 can be coincident with the central axis of the opening of the encompassing member 10. The outer edge 13b of support band 13 can contact a top surface of the knob 530 to prevent the ratchet tool 1 from sliding too far downward over the knob 530. This structural relationship can also maintain or lock the relative height position (position of the ratchet 1 along the rotational axis of the knob 530) through the force of gravity or through the application of downward force on the ratchet tool 1 to keep the outer edge 13b in contact with the top surface of knob 530.

Figure 8:
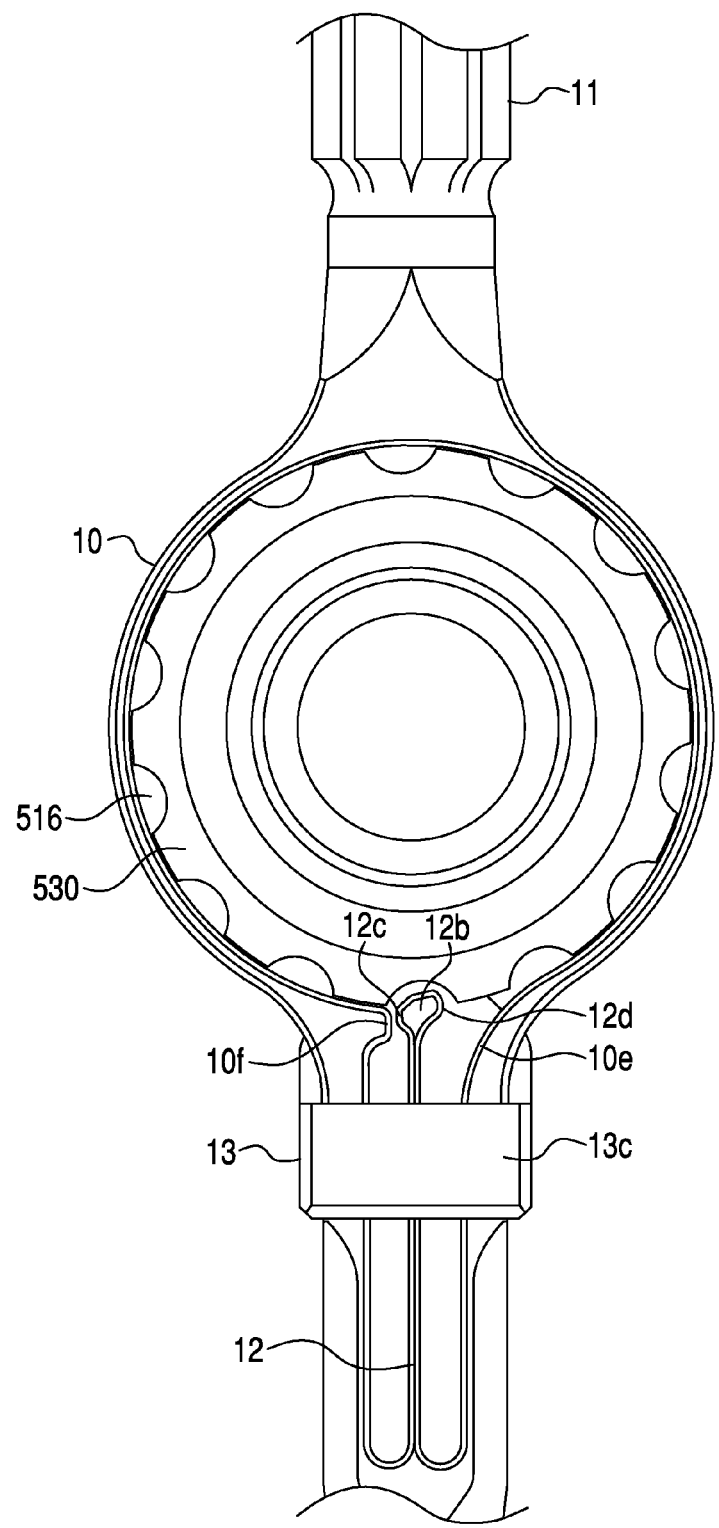
FIG. 8 is a bottom detailed view of the ratchet tool of FIG. 7 in use.

FIG. 8 shows an example of the operational arrangement of the pawl 12 with respect to the knurled surface 516 of the knob 530. When the knob 530 is located in the opening defined by the encompassing member 10 of the ratchet 1, the head 12b of pawl 12 is located within and engages with a scalloped or knurled surface 516 of the knob 530. Thus, when the ratchet 1 is rotated in a counterclockwise fashion (as viewed in FIG. 8) about the central axis of the opening of the encompassing member 10, the knurled surface 516 of knob 530 will engage the rounded distal end 12d of pawl 12 and the pawl 12 will be forced by this contact to move (or attempt to move) in a counterclockwise fashion (substantially to the left as shown in FIG. 8). This movement (or attempted movement) will be prevented by the contact surface 12c of the pawl 12 contacting or engaging with the opposing contact surface 10f of the encompassing member 10. The sandwiching contact between the pawl 12, knob 530 and encompassing member 10 will prevent movement of the knob 530 with respect to the encompassing member 10

(locking the knob 530 with respect to the ratchet tool 1). Thus, the nut or knob 530 will be forced to rotate with the encompassing member 10 and ratchet tool 1 in the counter-clockwise direction, and torsional force can be transferred from the ratchet tool 1 to the knob 530.

By contrast, when the ratchet tool 1 is rotated in a clockwise fashion (as viewed in FIG. 8) about the central axis of the opening defined by the encompassing member 10 of the ratchet tool 1, the knurled surface 516 will contact the detent or distal end 12d of the pawl 12 to cause the pawl to move clockwise (substantially to the right in FIG. 8) relative to the encompassing member 10. However, the opposing rounded surface 10e of the encompassing member can be configured such that the pawl can move freely in the clockwise/rightward direction. Eventually, the head 12b of pawl 12 slip out of the knurled surface 516 and ride along an outer peripheral surface of the knob 530 to an adjacent knurled surface 516 (thus, ratcheting between knurled surfaces). This action allows the ratchet tool 1 to rotate with respect to the knob 530 without applying substantial torsional force to the knob 530. In other words, the knob 530 can remain stationary with respect to the downtube and will not impart a force on any structure attached thereto (e.g., won't transfer torsional force to translation movement of an attached persuader structure).

The pawl 12 can have a longitudinal axis that intersects with the longitudinal axis of the encompassing member 10 (when the longitudinal axis is extended to cross the access-way defined between the rounded surface portion 10e and contact surface portion 10f). At least a portion of the head 12b of pawl 12 is located on an interior side of a cylindrical plane that contains the inner peripheral surface of the encompassing member that extends between the rounded surface portion 10e and the contact surface portion 10f. At least a portion of the spring structure 12a can be located on an exterior side of the same cylindrical plane with respect to the encompassing member 10.

Figure 9A:
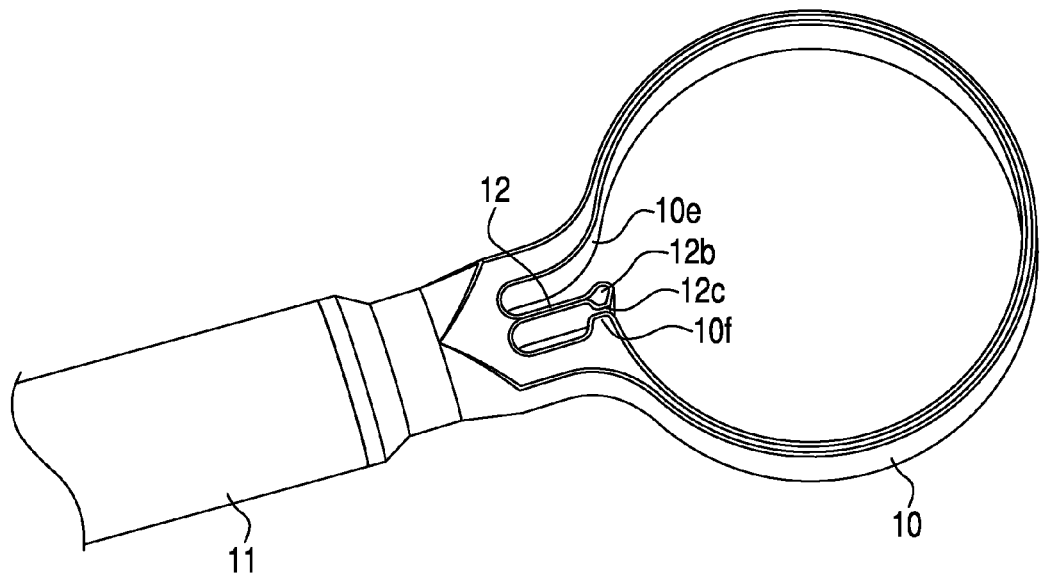
FIG. 9A is a perspective view of another embodiment of a ratchet tool made in accordance with principles of the disclosed subject matter.

FIG. 9A is a perspective view of another embodiment of a ratchet tool 1. In this embodiment, a single handle 11 extends from an outer periphery of the encompassing member 10. Band 13 is not present in this embodiment and instead, each of the pawl 12, handle 11, and encompassing member 10 can be made from a thicker or stronger material relative to the embodiments that include band 13. Otherwise, the pawl 12, handle 11, and encompassing member 10 can be configured similar to those of the embodiments described above.

Figure 9B:
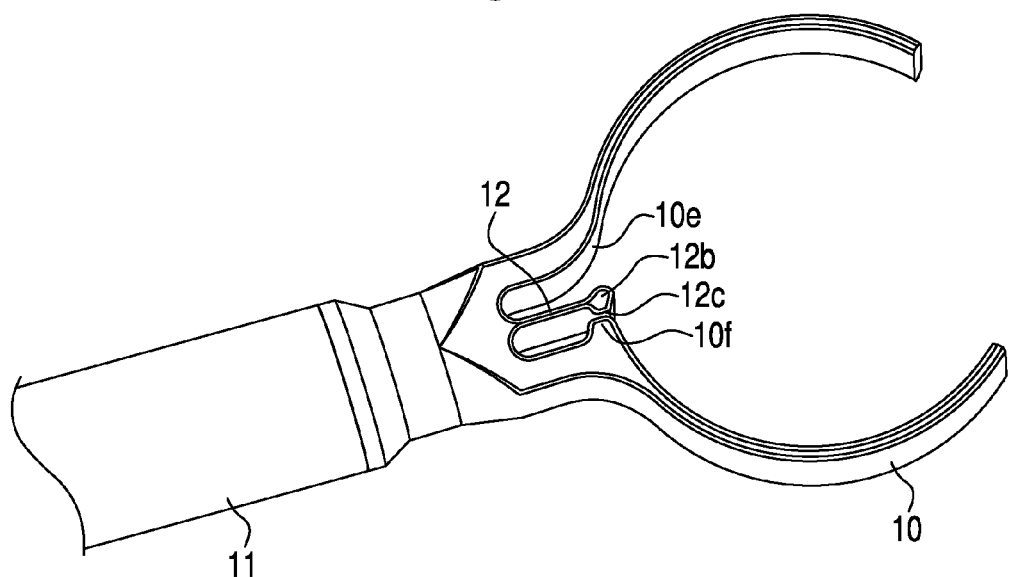
FIG. 9B is a perspective view of another embodiment of a ratchet tool made in accordance with principles of the disclosed subject matter.

FIG. 9B is a perspective view of another embodiment of a ratchet tool 1. The encompassing member 10 in this embodiment is an example of an open configuration in which the encompassing member 10 does not extend completely around. In this example, the encompassing member 10 is formed in a substantial C-shape defined by a first arm and a second arm, each arm extending symmetrically away from the pawl 12 and handle 11. Of course, non-symmetrical versions of this tool are contemplated where different shaped arms extend away from pawl 12 and/or handle 11. Likewise, the opening in the encompassing member 10 can be located at different locations about the periphery of the encompassing member 10. In addition, multiple handles 11 and/or pawls 12 can be used with the concept of an open configuration for the encompassing member 10.

FIG. 10 is a perspective view of another embodiment of a ratchet tool 1 and knob 530 made in accordance with principles of the disclosed subject matter. In this embodiment, the encompassing member 10 can be configured to take a non-symmetrical shape as viewed from a point located above and along a central axis of the encompassing member 10. In addition, the nut, or knob 530, can be non-symmetrical as viewed from this same vantage point. Although the contact portion 10f is shown as spaced from the head 12b of pawl, the contact portion 10f can conceivably extend.

FIG. 11 is a perspective view of another embodiment of a ratchet tool 1 and knob 530 made in accordance with principles of the disclosed subject matter. In this embodiment, the encompassing member 10 can be configured to take a polygonal shape (such as a triangle) as viewed from a point located above and along a central axis of the encompassing member 10. In addition, the knurled surface 516 and head 12b can be configured to have angular mating surface. In particular, the knurled surface 516 can include a plurality of v-shaped grooves located along an outer peripheral surface of knob 530 and which run substantially parallel with the rotational axis of the knob 530. The head 12b of the pawl can thus also be V-shaped. The contact surface 12c of the head 12b of pawl 12 can extend substantially towards the encompassing member 10. In addition, the contact surface portion 10f of the encompassing member 10 can be configured as a rounded indent in the inner peripheral surface 10b of the encompassing member 10. The indent can perfectly match the rounded extent of the contact surface 12c. This configuration may facilitate a closer tolerance and little or no gap between the contact surface 12c of the pawl 12 and the encompassing member 10. For example, the different shape (triangle shape) of the encompassing member 10 may allow for machining or heat manipulation of the ratchet tool 1 after molding the tool 1 such that the contact surface 12c of pawl 12 and the encompassing member 10 can be brought closer together (or in contact) as compared to their orientation after the structure is molded. Such modifications may reduce any play associated with the ratchet action.

FIG. 12 is a perspective view of another embodiment of a ratchet tool 1 and knob 530. In this embodiment, the knob 530 can be provided with a stop ring 531 located about an upper and outer periphery of the knurled surface 516. The stop ring 531 can define a plane upon which a bottom surface 10d of the ratchet tool 1 can sit during operation of the system 800. Thus, the upper edge 13b of band 13 is not necessary in this embodiment to set or lock the location between the knob 530 and ratchet tool 1. Furthermore, the stop ring 531 could permit the ratchet tool 1 to be made without the band 13 altogether.

Figure 13:
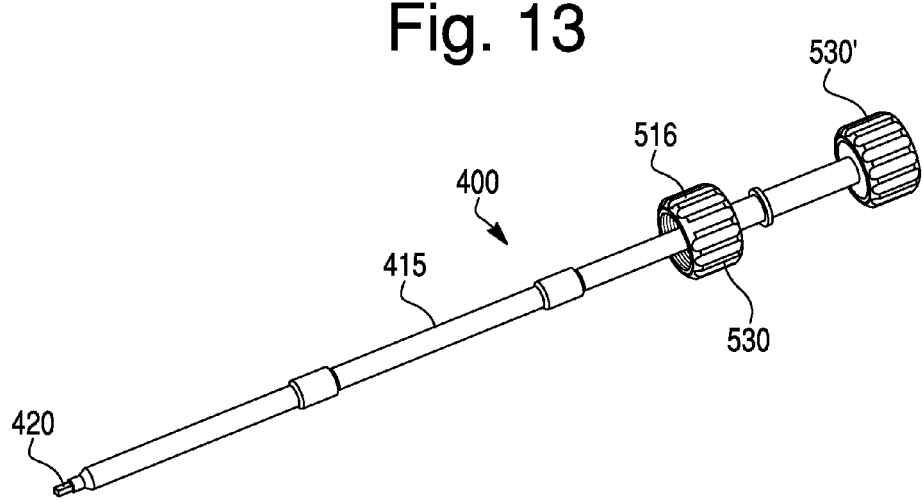
FIG. 13 is a perspective view of another embodiment of a portion of a system, including a screw driver, made in accordance with principles of the disclosed subject matter.
Figure 14:
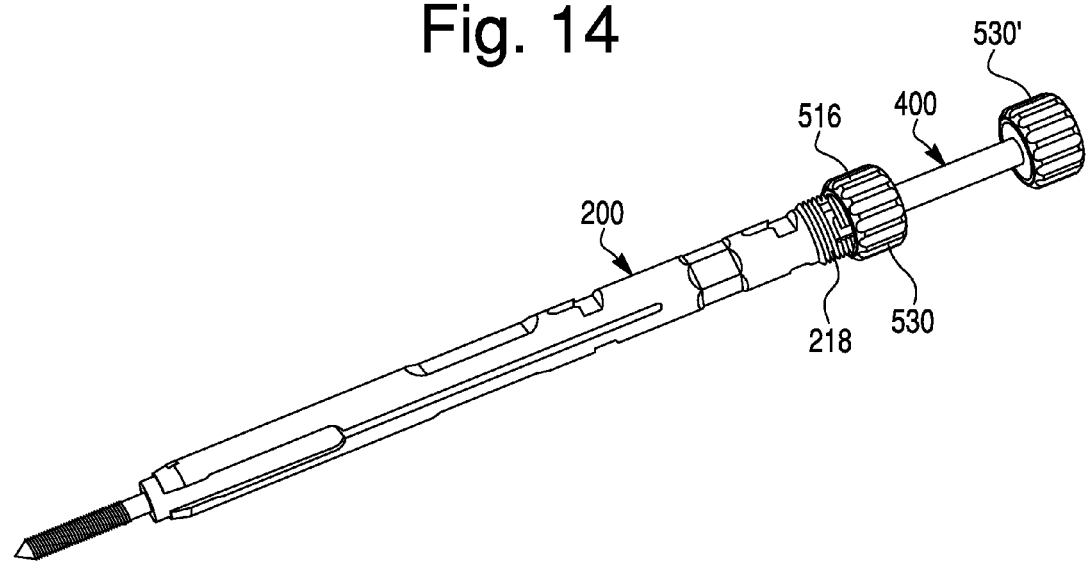
FIG. 14 is a perspective view of the portion of the system of FIG. 13 including a downtube when in use.

FIGS. 13 and 14 show an exemplary system in which a screw driver 400 can be coupled to the downtube 200 such that the screw driver is driven by a ratchet tool 1. Screw driver 400 can include a proximal end 410, a distal end 420 and a shaft 415 extending between the proximal and distal ends. A hollow cylindrical knob 430 can be mounted on shaft 415. Knob 430 is rotatable about shaft 415, and includes a knurled exterior surface 416 and an interior surface 417. The knurled surface 416 can interact with the ratchet tool 1 in the same or similar way as compared to knurled surface 516 and knob 530 described above. Interior surface 417 of knob 430 can include an inner thread 418 adapted to engage with outer thread 218 on downtube 200. Once screw driver 400 is inserted into passage 230 of downtube 200, knob 430 can be screwed down over the proximal end 210 of the downtube to rigidly attach and lock the screwdriver to the downtube, with substantially no toggle or play. The screw driver shaft 415 can be coaxially aligned with the longitudinal axis L of downtube 200, and remains free to rotate relative to the downtube. The screw driver shaft 415 can include knob 530' located at an end thereof such that ratchet tool 1 can also be used to apply torque to the screw driver 400.

Figure 15:
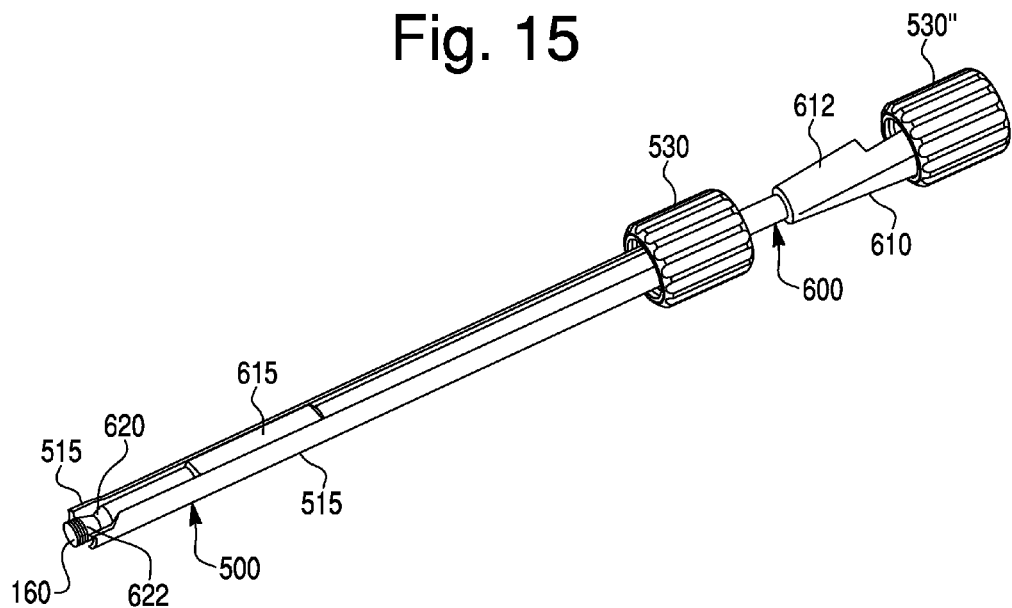
FIG. 15 is a perspective view of another embodiment of a portion of a system, including a rod persuader and set screw inserter, made in accordance with principles of the disclosed subject matter.
Figure 16:
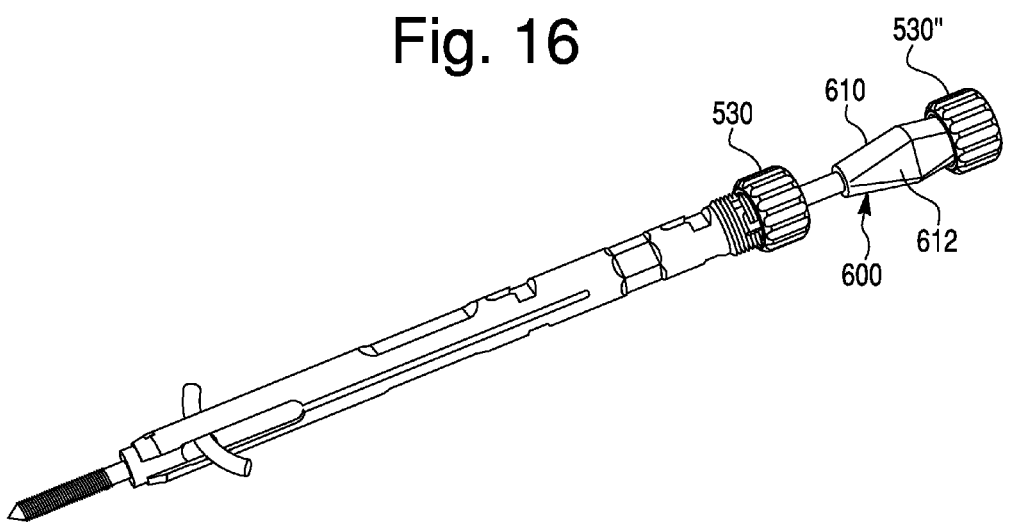
FIG. 16 is a perspective view of the portion of the system of FIG. 15, including a downtube, when in use.

FIGS. 15 and 16 show the rod persuader 500 when used with a set screw inserter 600 carrying a set screw 160 within downtube 200. Ratchet tool 1 can be used in this system to drive both the rod persuader 500 and the set screw inserter 600. Set screw inserter 600, which is separate from rod persuader 500, has a proximal end 610 forming a handle 612 and a distal end 620 having a tip 622 that carries the set screw 160. A shaft 615 extends between the proximal end 610 and distal end 620. Set screw inserter 600 may be inserted into downtube 200 after rod persuader 500 is attached to the downtube and engaged with the rod 150. In operation, the set screw inserter 600 is inserted between the pusher members 515 of rod persuader 500, and advanced axially into downtube 200. Set screw inserter 600 is advanced into passage 230 to place set screw 160 into a threaded opening 111 of a screw assembly 110. Once the set screw 160 is properly positioned at the threaded opening 111, handle 612 can be rotated to rotate the shaft 615 and set screw 160 to drive the set screw into the threaded opening of the screw assembly 110. An additional knob 530" can be located at the proximal end of shaft 615 such that ratchet tool 1 can be used to apply additional torque to the set screw inserter 600, if/when desired.

Methods for using a ratchet tool 1 can vary widely depending on the user's preference and the type of surgery. In one example, a user or surgeon will begin a surgical procedure (invasive procedure, non-invasive procedure, medical procedure, etc.), such as alignment and/or implantation of a spinal rod. During the surgical procedure, downtubes 200 can be located adjacent and in contact with bone screws that carry a spinal rod. A persuader 500 can be located within the downtube 200 and in contact with the spinal rod. The persuader 500 can have a nut, e.g., knob 530, that includes at least one ratchet indent located on an outer periphery. A surgical wrench can be provided which has a main body 10 with an inner peripheral surface 10*b* defining an opening having a central axis. The main body can include a pawl 12 that extends into the opening of the main body of the surgical wrench 1. The surgical wrench 1 can be placed onto the knob 530 of the persuader 500 during surgery, such that the knob 530 is located within the opening of the surgical wrench 1. The user can operate the wrench 1 by directly contacting the at least one ratchet indent of the knob 530 with the pawl 12 of the surgical wrench 1 and rotating the surgical wrench 1 such that the knob 530 rotates with the surgical wrench 1 in a first rotational direction, and rotating the surgical wrench in a second rotational direction opposite to the first rotational direction while causing the pawl 12 to flex or bias with respect to at least one of the main body 10 and the knob 530 such that the surgical wrench 1 rotates with respect to the knob 530. By this action, the knob 530 can be easily rotated in a limited space and with a relatively large amount of torque, thus causing the persuader 500 to manipulate a spinal rod in accordance with the user or surgeon's desire. Of course, several variations of the method are available to the surgeon, and the steps outlined above are not necessarily sequential or necessary, but merely exemplary.

While certain embodiments of the disclosed subject matter are described above, it should be understood that the disclosed subject matter can be embodied and configured in many different ways without departing from the spirit and scope of the disclosure. For example, any of the structures related to the configuration of the knob 530, the encompassing member 10, the handle 11, and the pawl 12 can be interchangeably associated with the other embodiments in combination or in replacement with each other. For example, any of the disclosed embodiments can include two (or more) handles 11. Likewise, any of the embodiments can conceivably include a single handle 11. Each of the embodiments can also include the pawl 12 or the encompassing member 10 from any of the other disclosed or contemplated embodiments. In addition, although the nut is disclosed as a knob 530 in each of the depicted embodiments, any of the disclosed or contemplated embodiments can include a nut that is shaped differently.

In particular, the nut can be much smaller in shape when the ratchet tool 1 is attached directly to a surgical device other than downtube 200 (such as to a bone screw, surgical implant, or other surgical tool). The nut could conceivably be non symmetrical in cross-section and could be a spline built into an elongate member. The knurled surface 516 can also be formed in many various ways without falling outside the scope of the presently disclosed subject matter. For example, the knurled surface 516 can be formed as a plurality of dimples located about an outer periphery of the nut or surgical device that is being driven by the ratchet tool 1. The dimples can be semi-spherical or other shape that matches or engages well with an outer geometry of the head 12*b* of pawl 12. It is also contemplated that the knurled surface 516 can act as a key for working with the ratchet tool 1, such that the ratchet tool 1 only works at a particular location on the driven surgical device.

With regard to the pawl 12, various different shapes, configurations and structures are contemplated. For example, the pawl can include a spring portion 12*a* that is not linear in shape and instead is a bent type of leaf spring extending from or attached to an interior side section of the handle 11. The spring portion 12*a* can also be configured in other known manners that would provide the flexibility or biasing for the head 12*b* of the pawl 12 to engage and disengage with the nut, such as in the form of a coil spring or even piston type structure. The head 12*b* of pawl 12 can also be separately configured with a ball or roller bearing that rolls over the exterior surface of the nut.

The encompassing member 10 can be configured and shaped in many various and different ways. Closed loop and open loop configurations are contemplated, and the shape can take on many various symmetrical and non-symmetrical forms as viewed along the central axis of the opening. For example, the inner peripheral surface of the encompassing member 10 can be completely cylindrical with a window therein in which the pawl 12 resides. Alternatively, the encompassing member can include a plurality of pawls 12 located about a perimeter of the inner peripheral surface. The pawl 12 can be built into the handle 11 or can be built into a separate structure or the wall of the encompassing member 10 itself, if thickness allows.

The band 13 can also be configured in many different ways or eliminated from the structure of the ratchet tool 1 altogether. For example, the band can be configured as simple reinforcement ribs placed at locations that would buttress or support the structural integrity of the handle or the structural integrity of the encompassing member, or both. By contrast, the band 13 can be configured as a large structure that caps the entire encompassing member, to create a cup like structure.

With regard to the method for manufacturing the disclosed subject matter, the ratchet tool 1 can be molded in its entirety from a single material to provide a device that can be easily sterilized and easily manufactured. For example, the a mold cavity can be created that includes a cavity portion for the encompassing member 10, a cavity portion for the handle 11, and a cavity portion for the pawl 12, wherein the cavity portion for the pawl resides substantially within the cavity portion for the handle. If a band 13 is desired, it can be separately welded to the handle 11 and/or encompassing member 10, or conceivable can be incorporated into the mold cavity depending on the specific geometry of the band 13. The band 13 could take the form of a cap or disc structure that is molded with and that completely encloses the top opening of the encompassing member 10. In this contemplated embodiment, the ratchet tool 1 would appear more like a spoon or cup that, when in use, is turned upside down and placed over a nut. The bottom of the cup, or disc structure of the band 13, would contact a top surface of the nut and limit or lock the location of the ratchet tool 1 with respect to the nut.

The method of manufacturing the ratchet tool 1 can also include machining the ratchet tool 1 from a single block or piece of material. Alternatively, different portions of the ratchet tool 1 can be separately machined. For example, the band 13 can be machined separately from the encompassing member 10, handle 11, and pawl 12, and then later welded or otherwise attached to the handle 11 and/or encompassing member 10. Laser, wire brush, hydraulic, die cut and other types of machining are contemplated for use in the disclosed subject matter.

It is also contemplated that the handle(s) 11 can be configured in many and various different ways. For example, the handle 11 can be formed as a plurality of wave like undulations or star like projections that extend from an outer peripheral surface 10a of the encompassing member 10. The handles 11 are shown as having a longitudinal axis that is straight and intersects with the central axis of the opening of the encompassing member 10. However, the longitudinal axis could be angled (at a non-acute angle) with respect to the optical axis in one or two planes orthogonal to each other and the central axis. Thus, one or more handles 11 can be curved or angled outside of a plane containing the top or bottom surface of the encompassing member 10. The handle(s) 11 are shown as being an integral portion of the encompassing member 10, but could also be separate parts that are attached to the encompassing member 10 at the discretion of the user. For example, a threaded extension can be formed on the outer peripheral surface of encompassing member 10 for attaching a handle or handles when desired.

The material selected for use in any of the components of the system 800 can be selected from well known biocompatible and surgical device materials. For example, any or all components of the system can be made from titanium, stainless steel, aluminum, other metal or metal alloys, plastics, ceramics, shape memory materials and other materials. The ratchet tool 1 can be made of the same material as a nut, such as knob 530, or can be made from different material if different rigidity or tactile feedback is desired.

The exemplary method described above relates to the use of a persuader 500 for a spinal rod. However, the wrench or ratchet tool 1 can be used in various other surgical procedures including but not limited to applying torque to a surgical bone screw, applying torque to a set screw, applying force to other types of bone rods or plates, and other procedures.

While the subject matter has been described in detail with reference to exemplary embodiments thereof, it will be apparent to one skilled in the art that various changes can be made, and equivalents employed, without departing from the scope of the invention. All related art references described in above are hereby incorporated by reference in their entirety.

What is claimed is:

1. A surgical ratchet, comprising: an encompassing member having an inner peripheral surface defined by an opening, and an outer peripheral surface opposed to the inner peripheral surface; a first handle extending away from the outer peripheral surface of the encompassing member, the handle having a proximal end and a distal end opposite the proximal end with a longitudinal axis extending therebetween, the distal end of the first handle being connected to the outer peripheral surface of the encompassing member; and a pawl having a fixed end attached to the distal end of the first handle, the pawl extending away from the first handle and extending into the opening which is defined by the inner peripheral surface and the distal end of the first handle, the pawl having a biased portion and a head located at a free end opposite the fixed end, the biased portion of the pawl disposed between first and second opposing portions of the inner peripheral surface, the biased portion including a spring portion that is contiguous with the head, wherein the spring portion extends from the fixed end to the free end, and wherein the spring portion extends through a channel formed between opposing walls of the handle, the channel being coaxial with the longitudinal axis of the handle, and wherein the head is movable with respect to at least one of the first handle and encompassing member; wherein a portion of the opening adjacent the distal end of the handle includes a contacting portion and a rounded surface opposing the contacting portion, wherein the head of the pawl includes a contact surface that faces and is configured to engage the contacting portion of the opening, wherein the head of the pawl is adjacent to and spaced away from the rounded surface, wherein the rounded surface extends away from the head of the pawl, and wherein the inner peripheral surface and the rounded surface are a continuously smooth, curved surface.

2. The surgical ratchet of claim 1, wherein the biased portion of the pawl is equidistant from the first and second opposing portions of the inner peripheral surface.

3. The surgical ratchet of claim 1, further comprising a second handle extending away from the outer peripheral surface of the encompassing member.

4. The surgical ratchet of claim 1, wherein the head of the pawl comprises a detent portion extending toward an engaging portion defined on the first opposing portion of the inner peripheral surface.

5. The surgical ratchet of claim 4, wherein a distance between the engaging portion and the longitudinal axis of the first handle is less than a distance between the first opposing portion and the longitudinal axis of the first handle.

6. The surgical ratchet of claim 4, wherein a distance between the engaging portion and the longitudinal axis of the first handle is greater than a distance between the first opposing portion and the longitudinal axis of the first handle.

7. The surgical ratchet of claim 4, wherein the engaging portion extends into the opening.

8. The surgical ratchet of claim 1, wherein the head of the pawl comprises a detent portion and a contact portion, the detent portion opposing the first opposing portion of the inner peripheral surface.

9. The surgical ratchet of claim 8, wherein a longitudinal axis of the head extends between the detent portion and the contact portion, and the longitudinal axis of the head intersects the longitudinal axis of the first handle.

10. The surgical ratchet of claim 1, further comprising a band extending over the head of the pawl and the opening.

11. The surgical ratchet of claim 1, wherein the encompassing member is formed so as to define in a cross-section a circular portion, a polygonal portion, or a non-symmetrical portion.

12. A surgical ratchet, comprising: an encompassing member having an inner peripheral surface defined by an opening, and an outer peripheral surface opposed to the inner peripheral surface; a first handle extending away from the outer peripheral surface of the encompassing member, the handle having a proximal end and a distal end opposite the proximal end with a longitudinal axis extending therebetween, wherein a portion of the opening adjacent the distal end of the handle includes a contacting portion and a rounded surface opposing the contacting portion; and a pawl having a fixed end attached to the first handle at a location intermediate the proximal and distal ends of the first handle, the pawl extending into the opening which is defined by the inner peripheral surface and the first handle, the pawl being substantially linear and extending along a longitudinal axis of the surgical ratchet, the pawl having a biased portion and a head located at a free end opposite the fixed end, the biased portion of the pawl disposed between first and second opposing portions defined at the distal end of the first handle, wherein the first and second opposing portions extend from the contacting portion and the rounded portion, respectively, such that the first and second opposing portions of the first handle are connected to the inner peripheral surface of the encompassing member, and the distal end of the first handle are connected to the outer peripheral surface of the encompassing member at an outer surface of the first handle, wherein the head is movable with respect to at least one of the first handle and encompassing member, wherein the head of the pawl includes a contact surface that faces and is configured to engage the contacting portion of the opening, wherein the head of the pawl is adjacent to and spaced away from the rounded surface, wherein the rounded surface extends away from the head of the pawl, and wherein the rounded surface is convex relative to the head of the pawl.

13. The surgical ratchet of claim 12, wherein the biased portion of the pawl is equidistant from the first and second opposing portions of the first handle.

14. The surgical ratchet of claim 12, further comprising a second handle extending away from the outer peripheral surface of the encompassing member.

15. The surgical ratchet of claim 12, wherein the head of the pawl comprises a detent portion extending toward an engaging portion defined at a junction of the first opposing portion and the inner peripheral surface.

16. The surgical ratchet of claim 15, wherein a distance between the engaging portion and the longitudinal axis of the first handle is less than a distance between the first opposing portion and the longitudinal axis of the first handle.

17. The surgical ratchet of claim 15, wherein a distance between the engaging portion and the longitudinal axis of the first handle is greater than a distance between the first opposing portion and the longitudinal axis of the first handle.

18. The surgical ratchet of claim 15, wherein the engaging portion extends into the opening.

19. The surgical ratchet of claim 15, wherein the head of the pawl comprises a detent portion and a contact portion, the detent portion facing the engaging portion.

20. The surgical ratchet of claim 15, wherein a longitudinal axis of the head extends between the detent portion and the contact portion, and the longitudinal axis of the head intersects the longitudinal axis of the first handle.

21. The surgical ratchet of claim 12, further comprising a band extending over the head of the pawl and the opening.

22. The surgical ratchet of claim 12, wherein the encompassing member is formed so as to define in a cross-section a circular portion, a polygonal portion, or a non-symmetrical portion.

23. A surgical ratchet tool, comprising: an encompassing member having an inner peripheral surface and an outer peripheral surface opposed to the inner peripheral surface, the inner peripheral surface being defined by a circular opening with a channel extending from a portion thereof, the channel having a channel entryway defined by a contacting portion and a rounded surface opposing the contacting portion; at least one handle extending from the outer peripheral surface of the encompassing member; and a pawl including a bias section coupled to the at least one handle and a head section extending from the bias section, the pawl having a pawl longitudinal axis that extends along the channel; wherein the head of the pawl includes a contact surface that faces and is configured to engage the contacting portion of the channel entryway, and wherein the head of the pawl is adjacent to and spaced away from the rounded surface, and wherein the rounded surface is further defined by an arcuate transition from the channel to the opening so that a distance between the rounded surface and a longitudinal axis of the channel continuously increases as the rounded surface extends towards the opening; and wherein a portion of the inner peripheral surface at the opening and the rounded surface form a continuously smooth, curved surface.

* * * * *